US012226324B2

United States Patent
Horne et al.

(10) Patent No.: US 12,226,324 B2
(45) Date of Patent: Feb. 18, 2025

(54) TRIAL NECK

(71) Applicant: DEPUY IRELAND UNLIMITED COMPANY, County Cork (IE)

(72) Inventors: David Horne, Leeds (GB); Thomas Maack, Leeds (GB); Jeffrey McAnelly, Columbia City, IN (US); Stephanie Prince, Leeds (GB); James Aaron Reed, Warsaw, IN (US); Duncan Young, Leeds (GB)

(73) Assignee: DEPUY IRELAND UNLIMITED COMPANY, LOUGHBEG INDUSTRIAL ESTATE, Co Cork (IE)

( * ) Notice: Subject to any disclaimer, the term of this patent is extended or adjusted under 35 U.S.C. 154(b) by 181 days.

(21) Appl. No.: 17/751,940

(22) Filed: May 24, 2022

(65) Prior Publication Data

US 2023/0081046 A1 Mar. 16, 2023

Related U.S. Application Data

(62) Division of application No. 16/640,431, filed as application No. PCT/EP2018/070454 on Jul. 27, 2018, now Pat. No. 11,369,492.

(Continued)

(51) Int. Cl.
*A61F 2/46* (2006.01)
*A61F 2/36* (2006.01)
*A61F 2/30* (2006.01)

(52) U.S. Cl.
CPC .......... *A61F 2/4684* (2013.01); *A61F 2/3609* (2013.01); *A61F 2/4607* (2013.01);
(Continued)

(58) Field of Classification Search
CPC ............ A61F 2/4684; A61F 2002/4044; A61F 2002/3652; A61F 2002/30616;
(Continued)

(56) References Cited

U.S. PATENT DOCUMENTS 4,306,550 A * 12/1981 Forte .................. A61B 17/1659
606/85
4,552,136 A * 11/1985 Kenna ................ A61B 17/1668
606/85

(Continued)

FOREIGN PATENT DOCUMENTS

| CN | 1193899 A | 9/1998 |
| CN | 106264797 A | 1/2017 |

(Continued)

OTHER PUBLICATIONS

European Search Report for Corresponding International Application No. PCT/EP2018070454, dated Mar. 1, 2019, 5 Pages.

(Continued)

*Primary Examiner* — Alvin J Stewart

(57) ABSTRACT

Kits and methods for use in intraoperative trialling of hip prostheses to determine an appropriate length for the femoral neck component of a prosthetic hip joint, are described. A kit for use in selecting a femoral neck component of an orthopaedic joint prosthesis kit comprises a first and a second broach. Each of the first and second broaches has a neck connection element comprising a projection extending from a proximal surface of the broach, each projection having a length. The projection on the first broach has a different length than the projection on the second broach. The kit also includes a trial femoral neck component having a neck connection element in the form of a recess in a distal surface. The recess is configured to mate with the projection on each of the first or second broaches such that mating of the trial femoral neck component with the first broach (Continued)

provides an assembly with a first neck length, and the mating of the trial femoral neck component with the second broach provides an assembly with a second neck length.

15 Claims, 6 Drawing Sheets

Related U.S. Application Data

(60) Provisional application No. 62/548,612, filed on Aug. 22, 2017.

(52) U.S. Cl.
CPC ............ *A61F 2002/30327* (2013.01); *A61F 2002/30331* (2013.01); *A61F 2002/3055* (2013.01); *A61F 2002/30616* (2013.01); *A61F 2002/30892* (2013.01); *A61F 2002/3625* (2013.01); *A61F 2002/365* (2013.01); *A61F 2002/3654* (2013.01)

(58) Field of Classification Search
CPC .. A61F 2002/30614; A61F 2002/30607; A61F 2/3609
See application file for complete search history.

(56) References Cited

U.S. PATENT DOCUMENTS

| | | | | |
|---|---|---|---|---|
| 4,587,964 | A * | 5/1986 | Walker | A61B 17/1659 606/85 |
| 4,962,155 | A | 10/1990 | Fujita | |
| 4,963,155 | A * | 10/1990 | Lazzeri | A61F 2/3609 606/85 |
| 5,041,118 | A | 8/1991 | Wasilewski | |
| 5,169,401 | A * | 12/1992 | Lester | A61B 17/1668 606/80 |
| 5,261,915 | A * | 11/1993 | Durlacher | A61B 17/1659 606/85 |
| 5,336,268 | A * | 8/1994 | Rispeter | A61F 2/3609 623/22.4 |
| 5,480,451 | A | 1/1996 | Grundei | |
| 5,569,263 | A | 10/1996 | Hein | |
| 5,645,607 | A * | 7/1997 | Hickey | A61F 2/4684 623/23.35 |
| 5,653,764 | A * | 8/1997 | Murphy | A61F 2/3609 623/23.15 |
| 5,766,261 | A * | 6/1998 | Neal | A61B 17/1659 606/85 |
| 5,951,606 | A * | 9/1999 | Burke | A61B 17/175 623/23.15 |
| 6,042,611 | A | 3/2000 | Noiles | |
| 6,306,174 | B1 * | 10/2001 | Gie | A61F 2/3609 623/23.15 |
| 6,447,518 | B1 | 9/2002 | Krause | |
| 6,464,728 | B1 * | 10/2002 | Murray | A61F 2/4637 623/23.23 |
| 6,702,854 | B1 | 3/2004 | Cheal | |
| 7,135,044 | B2 | 11/2006 | Basslk | |
| 7,572,297 | B2 * | 8/2009 | Cheal | A61F 2/3662 623/22.43 |
| 7,641,698 | B1 | 1/2010 | Gibbs | |
| 7,981,161 | B2 | 7/2011 | Choi | |
| 8,048,167 | B2 | 11/2011 | Dietz | |
| 8,449,619 | B2 | 5/2013 | Metcalfe | |
| 8,506,642 | B1 * | 8/2013 | Lyren | A61F 2/3609 623/22.11 |
| 8,562,690 | B1 * | 10/2013 | Dickerson | A61F 2/367 623/22.44 |
| 11,344,437 | B2 * | 5/2022 | Bailey | A61B 17/1659 |
| 11,369,492 | B2 * | 6/2022 | Horne | A61B 17/1659 |
| 2004/0004186 | A1 | 1/2004 | Jiyan | |
| 2004/0064186 | A1 * | 4/2004 | McCleary | A61B 17/1659 623/18.11 |
| 2004/0116933 | A1 * | 6/2004 | White | A61B 17/1668 606/85 |
| 2004/0122440 | A1 | 6/2004 | Daniels | |
| 2004/0236341 | A1 | 11/2004 | Petersen | |
| 2004/0267372 | A1 * | 12/2004 | Vanasse | A61F 2/4684 623/22.11 |
| 2005/0107799 | A1 | 5/2005 | Graf | |
| 2005/0143828 | A1 | 6/2005 | Collins | |
| 2005/0203634 | A1 * | 9/2005 | Bassik | A61F 2/4014 623/22.46 |
| 2005/0245934 | A1 | 11/2005 | Tuke | |
| 2006/0241625 | A1 * | 10/2006 | Metcalfe | A61B 17/162 606/79 |
| 2007/0050039 | A1 | 3/2007 | Dietz | |
| 2007/0219641 | A1 * | 9/2007 | Dorr | A61F 2/30907 623/22.24 |
| 2008/0133023 | A1 * | 6/2008 | Schlotterback | A61F 2/4684 623/20.15 |
| 2008/0262626 | A1 | 10/2008 | Raugel | |
| 2009/0048682 | A1 | 2/2009 | Choi | |
| 2009/0054993 | A1 * | 2/2009 | Le Bon | A61F 2/4684 623/23.15 |
| 2010/0023014 | A1 * | 1/2010 | Romagnoli | A61B 17/1659 606/85 |
| 2010/0100193 | A1 * | 4/2010 | White | A61F 2/46 623/22.4 |
| 2010/0241239 | A1 | 9/2010 | Smith | |
| 2011/0009976 | A1 * | 1/2011 | Cruchet | A61F 2/36 623/22.46 |
| 2011/0035021 | A1 * | 2/2011 | Bergin | A61F 2/36 623/22.42 |
| 2011/0125285 | A1 * | 5/2011 | Ragbir | A61F 2/3609 623/23.15 |
| 2011/0224798 | A1 * | 9/2011 | Caillouette | A61F 2/36 623/22.11 |
| 2012/0010722 | A1 * | 1/2012 | Walter | A61F 2/3601 623/23.18 |
| 2012/0259423 | A1 | 10/2012 | Carr | |
| 2012/0290099 | A1 * | 11/2012 | Gibson | A61F 2/4637 623/20.11 |
| 2013/0079888 | A1 * | 3/2013 | Meulink | A61F 2/3609 623/22.42 |
| 2013/0158674 | A1 | 6/2013 | Chow et al. | |
| 2013/0144397 | A1 | 10/2013 | Smith | |
| 2013/0261762 | A1 | 10/2013 | Kennedy | |
| 2014/0012392 | A1 * | 1/2014 | Walter | A61F 2/3601 623/23.26 |
| 2014/0276850 | A1 * | 9/2014 | Chaney | A61F 2/461 606/84 |
| 2014/0276866 | A1 | 9/2014 | Endsley | |
| 2015/0039093 | A1 * | 2/2015 | McTighe | A61F 2/3609 623/23.14 |
| 2016/0030200 | A1 * | 2/2016 | Hunt | A61F 2/3662 623/20.35 |
| 2016/0175109 | A1 * | 6/2016 | Reu | A61F 2/36 606/85 |
| 2016/0235417 | A1 * | 8/2016 | Duncan | A61B 17/1659 |
| 2016/0302803 | A1 * | 10/2016 | Macke | A61B 17/1668 |
| 2018/0303495 | A1 * | 10/2018 | Hirt | A61B 17/1659 |
| 2019/0099191 | A1 * | 4/2019 | Huff | A61B 17/1617 |
| 2019/0247063 | A1 | 8/2019 | Huff | |
| 2019/0336145 | A1 * | 11/2019 | Bader | A61B 17/1659 |
| 2020/0222208 | A1 * | 7/2020 | Bushell | A61F 2/34 |
| 2020/0268527 | A1 * | 8/2020 | Maniar | A61F 2/367 |
| 2020/0276029 | A1 * | 9/2020 | Bailey | A61B 17/1659 |
| 2020/0352742 | A1 * | 11/2020 | Horne | A61F 2/4684 |
| 2021/0093332 | A1 | 4/2021 | Walker | |
| 2021/0228219 | A1 * | 7/2021 | Clements | A61B 17/92 |
| 2021/0353433 | A1 * | 11/2021 | Huff | A61F 2/3609 |
| 2022/0031476 | A1 * | 2/2022 | Ait Si Selmi | A61F 2/4684 |
| 2022/0218489 | A1 * | 7/2022 | Anderson | A61F 2/3662 |
| 2023/0293315 | A1 * | 9/2023 | Shimeno | A61B 17/1659 623/22.12 |

(56) References Cited

U.S. PATENT DOCUMENTS

FOREIGN PATENT DOCUMENTS

| | | | | |
|---|---|---|---|---|
| DE | 102006031573 A1 * | 1/2008 | ............... | A61F 2/36 |
| DE | 102007032014 B3 | 10/2008 | | |
| EP | 1435223 A | 1/2004 | | |
| EP | 2027833 A1 * | 2/2009 | ........... | A61F 2/4684 |
| FR | 2574283 A | 6/1986 | | |
| FR | 2796267 A1 | 1/2001 | | |
| FR | 2865927 A1 * | 8/2005 | ........... | A61F 2/3609 |
| FR | 2889446 A1 * | 2/2007 | ............... | A61F 2/36 |
| GB | 806441 A | 3/1956 | | |
| JP | 2012165889 A * | 9/2012 | ........... | A61F 2/4684 |
| JP | 2013094331 A * | 5/2013 | ........... | A61F 2/4684 |
| JP | 5859810 B2 | 12/2015 | | |
| WO | WO1992003993 A1 | 9/1992 | | |
| WO | WO1996036284 A1 | 11/1996 | | |
| WO | WO2002026145 A1 | 4/2002 | | |
| WO | WO2009106866 A1 | 9/2009 | | |
| WO | WO2009108683 A1 | 9/2009 | | |
| WO | WO-2009111459 A2 * | 9/2009 | ......... | A61F 2/30734 |
| WO | 2012035294 A2 | 3/2012 | | |
| WO | WO-2012030409 A1 * | 3/2012 | ........... | A61F 2/3609 |
| WO | WO-2012034771 A1 * | 3/2012 | ........ | A61F 2/30771 |
| WO | WO2014140636 A1 | 9/2014 | | |
| WO | WO2014140639 A1 | 9/2014 | | |

OTHER PUBLICATIONS

Chinese Search Report for Corresponding China Application No. 201880054544.2, Document Identifying Mark: 310401, Feb. 2010, 3 Pages.
CN106264797 English Translation of Abstract.
D.H. Lucas Md, R.D_ Scott, MD, The Ranawat Sign, a Specific Maneuver to Assess Component Positioning in Total Hip Arthroplasty, Journal of Orthopaedic Techniques, vol. 2, No. Jun. 2, 1994, pp. 59-61.
CN1193899_Derwent Translation.
CN102048599_Derwent Translation.
FR2574283_Derwent Translation.
FR2796297_Derwent Translation.
JP5859810_Derwent Translation.

* cited by examiner

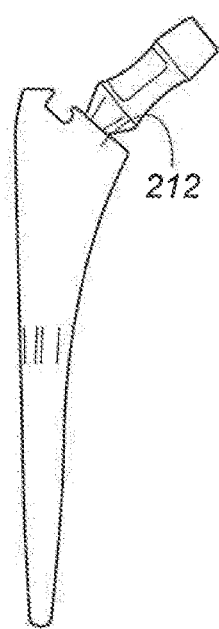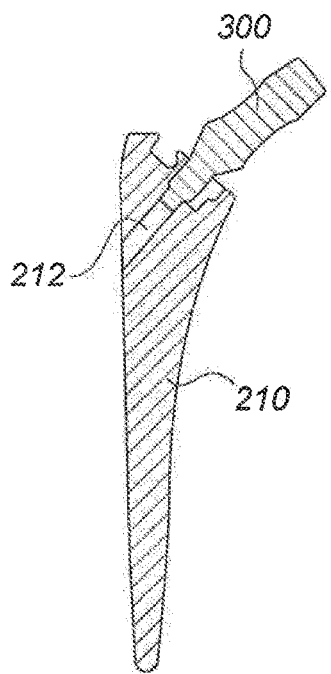
*Fig. 6a*  *Fig. 6b*
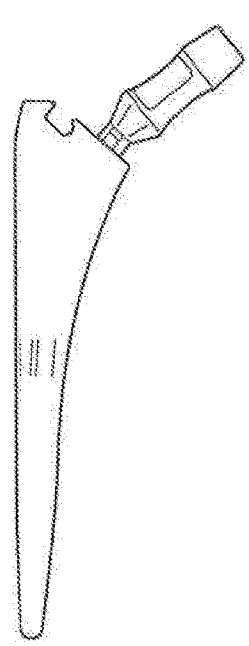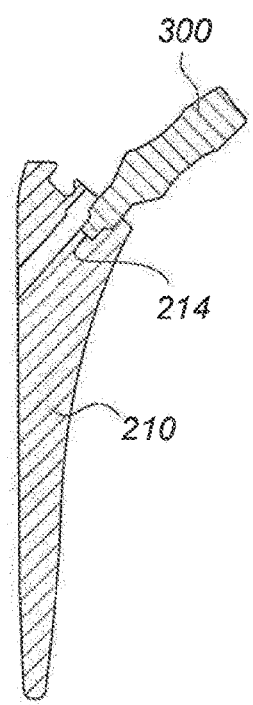
*Fig. 6c*  *Fig. 6d*

TRIAL NECK

CROSS-REFERENCE TO RELATED APPLICATIONS

This application is a Divisional of U.S. Pat. No. 11,369,492, filed on Feb. 20, 2020, which is a National Stage Application filed Under 35 U.S.C. § 371 of International Application No. PCT/EP2018/070454 filed Jul. 27, 2018, which claims priority to U.S. provisional 62/548,612 filed Aug. 22, 2017, all of which are hereby incorporated by reference in their entireties.

FIELD OF THE INVENTION

The present invention relates generally to the field of orthopedics, and more particularly to kits and methods for use in intraoperative trialling of hip prostheses to determine an appropriate length for the femoral neck component of a prosthetic hip joint.

BACKGROUND TO THE INVENTION

Optimal hip mechanics in hip arthroplasty is achieved through the selection of an appropriate neck length and head offset in the femoral component of the prosthetic hip implant.

The distance between the femoral stem component and the femoral head component, provided by the length of the neck of the femoral component, establishes the requisite head offset and neck length which in turn contributes to the desired range of motion, leg length, and tension in the soft tissue at the implant site. In order to optimize hip mechanics, it is desirable to select the leg length with precision. Femoral offset is an important clinical requirement. When offset is not restored, medialization of the femur can occur which results in impingement and possible instability. Additionally, if offset is not restored at the time of surgery, laxity of tissues can occur resulting in weakness and possible dislocation.

Conventionally, femoral stem components are offered in standard offset and high offset configurations to provide proper joint tension without affecting leg length or surgical technique.

Traditional implant stem geometry with a progressive neck length requires a different neck trial for each stem size and each offset variation. Trial femoral neck components are usually designed to work with the corresponding size of broach. This requires a large inventory of trial neck components within an instrument tray. In order to reduce the inventory, it would be desirable to reduce the number of trial femoral neck components required.

Advantageously, the instrument tray would include a set of broaches of varying sizes, one trial standard offset trial femoral neck component and one trial high offset femoral neck component.

SUMMARY OF THE INVENTION

The invention provides a kit in which progressive neck length is accommodated within the broach. This is achieved by the provision of a neck connection element on each size of broach that allows the neck length to be varied on the broach side of a broach/trial femoral neck assembly. This prevents the need for a different trial femoral neck component for each broach size. The inventory of trial femoral neck components within the instrument tray may therefore be reduced to one trial standard offset femoral neck component and/or one trial high offset femoral neck component.

Therefore, according to an aspect of the invention there is provided a kit for use in selecting a femoral neck component of an orthopaedic joint prosthesis, the kit comprising:

a first and a second broach, each of the first and second broaches having a neck connection element comprising a projection extending from a proximal surface of the broach, each projection having a length, the projection on the first broach having a different length than the projection on the second broach, and a trial femoral neck component having a neck connection element in the form of a recess configured to mate with the projection on each of the first or second broaches such that mating of the trial femoral neck component with the first broach provides an assembly with a first neck length, and in which the mating of the trial femoral neck component with the second broach provides an assembly with a second neck length.

In some constructions of the invention, the second broach is larger than the first broach, and the projection extending from the proximal surface of the second broach is longer than the projection extending from the proximal surface of the first broach. This results in the distal surface of the trial femoral neck component being spaced apart from the proximal surface of the first broach a first distance when the projection on the first broach is received within the recess of the trial femoral neck component. This also results in the distal surface of the trial femoral neck component being spaced apart from the proximal surface of the second broach a second distance when the projection on the second broach is received within the recess of the trial femoral neck component. As the second distance is greater than the first distance, the second broach provides an assembly with a longer neck length.

The kit may comprises more than two broaches. Each progressively larger size of broach has a corresponding longer projection. This enables the same trial femoral neck to be used with each broach within the kit, whilst still providing a progressively longer neck length as the broaches increase in size. This reduces the inventory of trial femoral neck components required.

The projection on each of the first and second broaches may be in the form of a post. A proximal portion of this post is configured to be received within the recess within the trial femoral neck component.

In some other constructions, the projection extending from the proximal surface of the broach has a portion that is configured to be received within the recess in the trial femoral neck component. In addition, the projection on at least one of the first and second broaches further comprises a platform that is provided adjacent to the proximal surface of the broach. When the trial femoral neck component is assembled with the broach, the platform acts to space a distal surface of the trial femoral neck component apart from the proximal surface of the broach. The platform therefore provides an assembly of a broach and trial femoral neck component that has a longer neck length than an assembly of a broach and trial femoral neck component in which the broach does not include the platform.

The projection on the first broach may consist only of the portion that is configured to be received within the recess in the trial femoral neck component. In comparison, the projection on the second broach also includes a platform. This platform effectively spaces the portion of the projection that is configured to be received within the recess in the trial femoral neck component away from the proximal surface of the second broach. The platform has length which is herein defined as the distance that the proximal surface of the platform is raised above the proximal surface of the broach. Consequently, when the trial femoral neck component is mated with the second broach the distal surface of the trial femoral neck component is spaced away from the proximal surface of the second broach by a distance equal to the length of the platform. As a result, the neck length of this assembly is longer than the neck length obtained when the trial femoral neck component is mated with the first broach.

In some constructions of the invention, the first broach also includes a platform. The platform on the second broach has a greater length than the platform on the first broach. Each of the platforms on the respective first and second broaches space the trial femoral neck component away from the proximal surface of the broach. However, because the length of the platform on the second broach is longer than the length of the platform on the first broach, the distal surface of the trial femoral neck component is spaced further away when the component is mated with the second broach than when it is mated with the first broach.

Kits may be provided that include a series of broaches (i.e., more than two broaches), with each broach in the series being progressively larger in size. For example, the kit may include at least a first broach, a second broach and a third broach. Each broach in the series (from smallest to largest) is provided with a successively longer platform, thereby providing a progressively longer leg length.

It is envisaged that the kit may comprise a single standard offset femoral neck trial component and a single high offset femoral neck trial component, with each being configured to be compatible for mating with the same projection on the proximal surface of each broach. This allows variation in the neck offset to be taken into account whilst also reducing the inventory of trial femoral neck components, when compared to conventional kits.

As mentioned above, it is advantageous to be able to account for the femoral neck offset required for each patient. To reduce the inventory required within the kit still further, in some embodiments a single trial femoral neck component is provided that has a first recess and a second recess laterally spaced apart on its distal surface. Each of the first and a second broaches within the kit has a projection that can be mated with either of the first and second recesses. The mating of the projection in the first recess of the neck component creates an assembly with a standard offset trial femoral neck component. The mating of the projection in the second recess of the neck component creates an assembly with a high offset trial femoral neck component. This enables the kit to include a single trial femoral neck component that is able to provide both a progressive neck length as the single trial femoral neck component is mated with progressively larger broaches, and additionally the ability to alter the neck offset dependent on the lateral position that the neck component is mated with the broach.

Advantageously, the projection or a portion thereof that extends from the proximal surface of each of the first and second broaches is preferably configured for connection with a broach handle. This enables easy removal of the broach from the femur.

According to a further aspect of the invention there is provided a method of selecting a femoral neck component for use in an orthopaedic joint prosthesis, the method comprising the step of:
 (i) using a kit comprising:
  a first broach and a second broach, each of the first and second broaches having a neck connection element comprising a projection extending from a proximal surface of the broach, each projection having a length, the projection on the first broach having a different length than the projection on the second broach, and
  a trial femoral neck component having a neck connection element in the form of a recess in a distal surface, the recess being configured to mate with the projection on each of the first or second broaches such that mating of the trial femoral neck component with the first broach provides an assembly with a first neck length, and in which the mating of the trial femoral neck component with the second broach provides an assembly with a second neck length;
 (ii) broaching a patient's femur using at least one of the first or second broaches;
 (iii) retaining the broach within the patient's femur;
 (iv) connecting the trial femoral neck component to the first broach or to the second broach;
 (v) connecting a trial femoral head component to the trial femoral neck component; and
 (vi) performing a trial reduction.

The kit used in the above-described method may comprise a standard offset femoral neck trial component and/or a high offset femoral neck trial component.

Some other kits for use in the method may consist of only a single trial femoral neck component. This component may comprise a first recess and a second recess, the second recess being laterally spaced from the first recess such that mating of the projection of either of the first or second broaches with the first recess provides an assembly with a trial neck component having a first horizontal offset, and mating of the same projection with the second recess provides an assembly with trial neck component having a second horizontal offset.

The first horizontal offset may be a standard offset femoral neck component. The second horizontal offset may be a high offset femoral neck component.

Therefore, according to a still further aspect of the invention there is provided a method of selecting a femoral neck component for use in an orthopaedic joint prosthesis, the method comprising the step of:
 (i) using a kit comprising:
  a broach having a neck connection element comprising a projection extending from a proximal surface of the broach, and
  a trial femoral neck component having a neck connection element in the form of a first recess and a second recess in a distal surface of the neck component, the recesses being laterally spaced apart, each recess being configured to mate with the projection on the broach, such that mating of the projection on the broach with the first recess on the trial femoral neck component provides an assembly with a first horizontal offset, and in which the mating of the projection on the broach with the second recess on the trial femoral neck component provides an assembly with a second horizontal offset;
 (ii) broaching a patient's femur using the broach;
 (iii) retaining the broach within the patient's femur;
 (iv) connecting the trial femoral neck component to the broach by mating the projection on the broach with one of the first recess or second recess on the trial femoral neck component to provide a trial femoral neck component with a first horizontal offset;
 (v) connecting a trial femoral head component to the trial femoral neck component; and
 (vi) performing a trial reduction.

Optionally, the method may further comprise the steps of:

(vii) disconnecting the trial femoral neck component from the broach;

(viii) reconnecting the trial femoral neck component to the broach by mating the projection on the broach with the other one of the first recess or second recesses on the trial femoral neck component to form a trial femoral neck component with a second horizontal offset;

(ix) connecting a trial femoral head component to the trial femoral neck component; and (x) performing a trial reduction.

For example, the mating of the projection in the first recess of the trial femoral neck component creates an assembly having a standard offset trial femoral neck component. In comparison, the mating of the projection in the second recess of the trial femoral neck component creates an assembly with a high offset trial femoral neck component.

When mating a trial femoral neck component with broaches it is desirable to be able to recreate the final implant geometry, thereby allowing more accurate feedback within range of motion testing. In the case of broaches having a male connection element (e.g., a recess) within a proximal surface and a trial femoral neck component having a femoral connection element (e.g., a projection) extending from the distal surface, the final implant geometry can be recreated by the provision of a trial femoral neck component that comprises a shaft having a longitudinal axis (the distal end of which is provided with the projection for mating with the broaches' recess) and a flared shoulder component. At least a portion of flared shoulder component is moveable along the longitudinal axis. The shoulder component has a first end and a second end, the second end being wider than the first end. The shoulder component is orientated on the shaft such that its wider end is distally located, thereby replicating the shoulder section of the final femoral neck.

In some embodiments, the shoulder component is cannulated and the entire shoulder component is slidable along the neck's shaft such that the wider distal end of the shoulder component is positionable adjacent to the proximal surface of the broach.

In some other embodiments, at least part of the shoulder section is extendable, to enable the wider distal end of the shoulder component to be moved along the longitudinal axis of the neck's shaft, and positioned adjacent to the proximal surface of the broach. For example, a distal portion of the shoulder component can include a concertina-like section, which can be extended in length to position the shoulder component adjacent to the proximal surface of the broach. This concertina-like section may be extended by the user, or by gravity, or by the action of a spring force.

According to a further aspect of the invention there is also provided a kit for use in selecting a femoral neck component of an orthopaedic joint prosthesis, the kit comprising, a broach having a neck connection element comprising a first recess and a second recess in a proximal surface of the broach, the first and second recesses being laterally spaced apart on the proximal surface of the broach, and a trial femoral neck component having a neck connection element comprising a projection at a distal end, the projection being configured to mate with each of the first and second recesses such that mating of the trial femoral neck component with the first recess provides an assembly with a first horizontal offset, and in which the mating of the trial femoral neck component with the second recess provides an assembly with a second horizontal offset.

For example, the mating of the projection in the first recess of the broach may create an assembly with a standard offset trial femoral neck component. In comparison, the mating of the projection in the second recess may create an assembly with a high offset trial femoral neck component.

This enables the kit to include a single trial femoral neck component that is able to provide both a standard offset and high standard offset trial options depending on the lateral position of the recess into which the neck component is mated with the broach.

According to a further aspect of the invention there is provided a method of selecting a femoral neck component for use in an orthopaedic joint prosthesis, the method comprising the step of:

(i) using a kit comprising:
  a broach having a neck connection element comprising a first recess and a second recess in a proximal surface of the broach, the first and second recesses being laterally spaced apart on the proximal surface of the broach, and
  a trial femoral neck component having a neck connection element comprising a projection at a distal end, the projection being configured to mate with each of the first and second recesses such that mating of the trial femoral neck component with the first recess provides an assembly with a first horizontal offset, and in which the mating of the trial femoral neck component with the second recess provides an assembly with a second horizontal offset, in which the second horizontal offset is different from the first horizontal offset;

(ii) broaching a patient's femur using the broach;

(iii) retaining the broach within the patient's femur;

(iv) connecting the trial femoral neck component to the broach by mating the projection on the trial femoral neck component with one of the first recess or second recess on the broach;

(v) connecting a trial femoral head component to the trial femoral neck component; and (vi) performing a trial reduction.

Optionally, the method may further comprise the steps of:

(vii) disconnecting the trial femoral neck component from the broach;

(viii) reconnecting the trial femoral neck component with the broach by mating the projection on the trial femoral neck component with the other one of the first recess or second recess on the broach;

(ix) connecting a trial femoral head component to the trial femoral neck component; and (x) performing a trial reduction.

DETAILED DESCRIPTION OF THE INVENTION

The invention will now be described, by way of example only, with reference to the following drawings, in which.

Figure 3A:
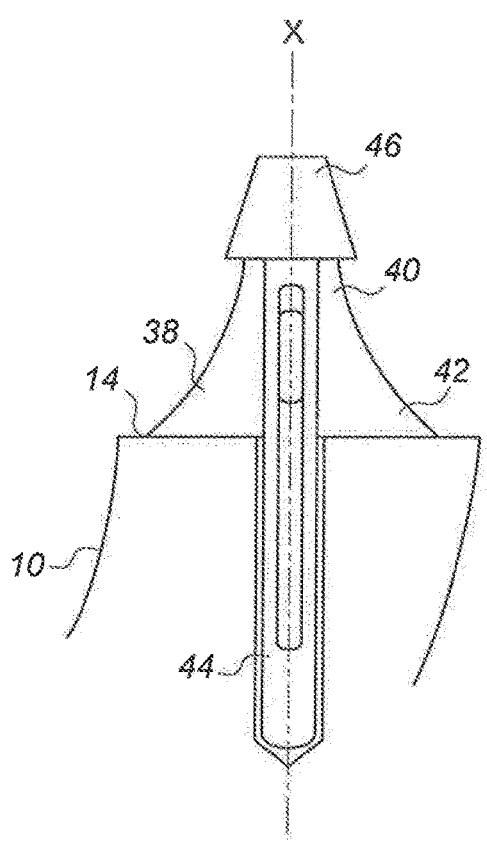

FIG. 3a: Shows a schematic of a first construction of a shoulder component in use with a size 0 broach FIG. 3b: Shows a schematic of a first construction of a shoulder component in use with a size 10 broach.

Figure 4A:
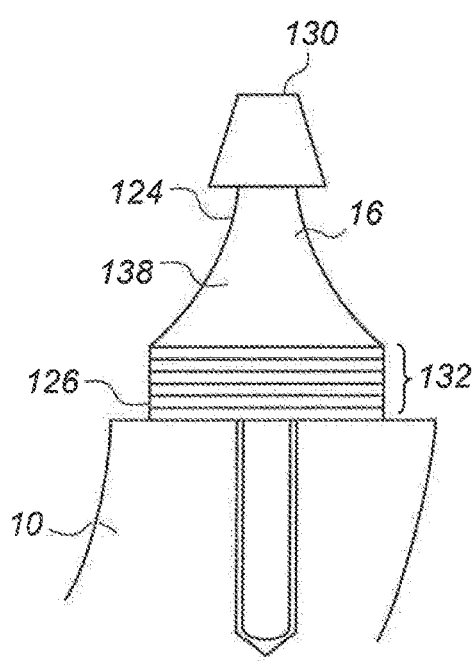

FIG. 4a: Shows a schematic of a second construction of a shoulder component in use with a size 0 broach FIG. 4b: Shows a schematic of a second construction of a shoulder component in use with a size 10 broach.

Figure 5:
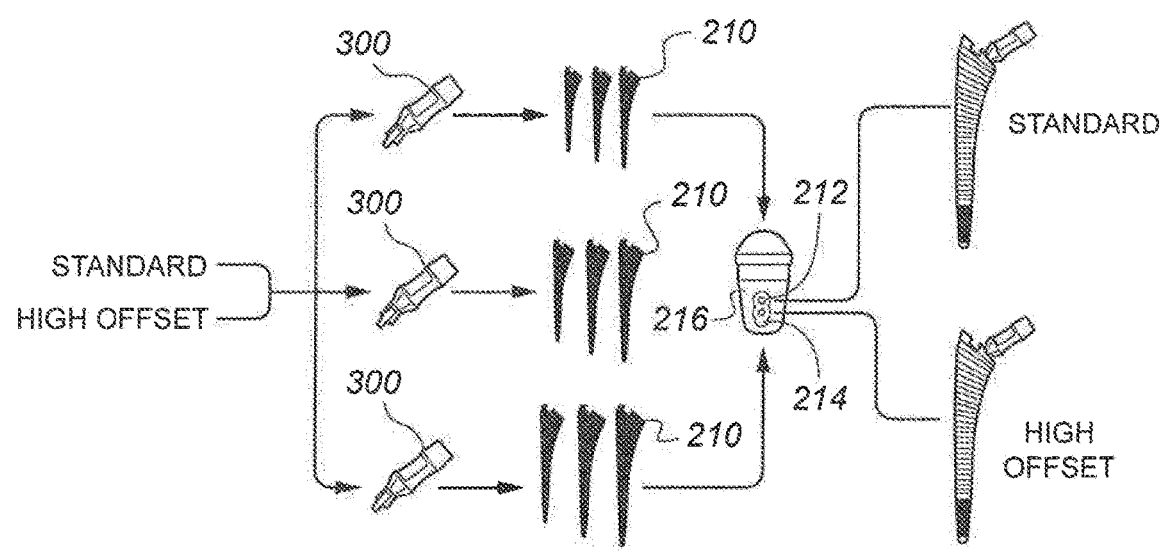

FIG. 5: Shows a schematic of three configurations of an instrument kit, with each configuration including three sizes of broach which can be used with a single trial femoral neck component to form either a standard or high offset.

FIG. 6a: Shows a side view of the mechanism of connection of the single trial femoral neck component to the broach to form a standard offset femoral neck component.

FIG. 6b: Shows a cross-sectional view of the mechanism of connection of the single trial femoral neck component to the broach to form a standard offset femoral neck component.

FIG. 6c: Shows a side view of the mechanism of connection of the single trial femoral neck component to the broach to form a high offset femoral neck component.

FIG. 6d: Shows a cross-sectional view of the mechanism of connection of the single trial femoral neck component to the broach to form a high offset femoral neck component.

Figure 1A:
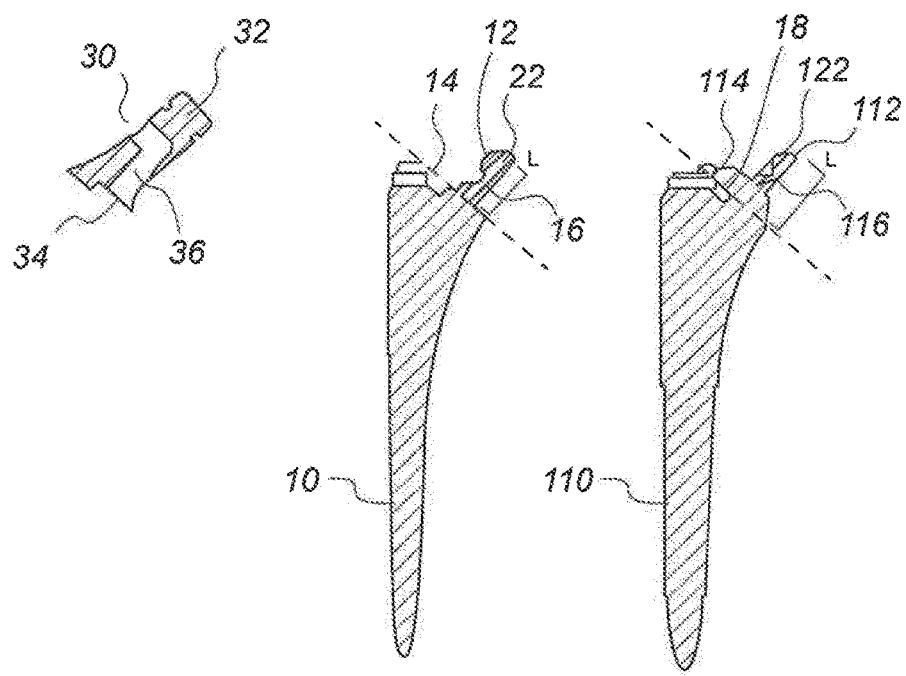
FIG. 1a illustrates the components of the kit that includes a size 0 broach, a size 10 broach and a standard offset trial femoral neck component.

FIG. 1(a) shows an exemplary construction of the kit of the invention that includes a first broach 10 of size 0, a second broach 110 of size 10 and a trial standard offset femoral neck component 30.

Each broach 10, 110 has a projection 12, 112 that extends from the proximal surface 14, 114 of the broach. In the first broach 10 the projection 12 consists of a post 16 extending from the broaches' proximal surface 14. In comparison, the projection 112 on the second broach 110 includes a post 116 that is spaced from the proximal surface 114 of the broach by a platform 18. The posts 16, 116 are the same length. The provision of the platform/post combination as shown for the second broach is advantageous over simply the provision of a longer post on the second broach, because the platform prevents soft tissue becoming trapped in the gap between the trial femoral neck component and the proximal surface of the second broach. Additionally, because the provision of the platform more accurately represents the final implant geometry, the surgeon is able to undertake more accurate range of motion assessments.

Each projection has a length (L). The length of the projection 12 on the first broach 10 is defined by the length of the post 16. The length of the projection 112 on the second broach 110 is defined by the combined length of the platform 18 and the length of the post 116.

The length of the projection 12 on the first broach 10 is shorter than the length of the projection 112 on the second broach 110.

Each projection 12, 112 has a proximally located detent 22, 122 that is configured for connection with a broach handle.

The trial standard offset femoral neck component 30 has a proximal surface 32 configured to mate with a trial femoral head component (not shown).

The trial standard offset femoral neck component 30 has a distal surface 34 which includes a recess 36 configured to mate with each of the projections 12, 112 on the first broach 10 and the second broach 110, respectively.

Figure 1B:
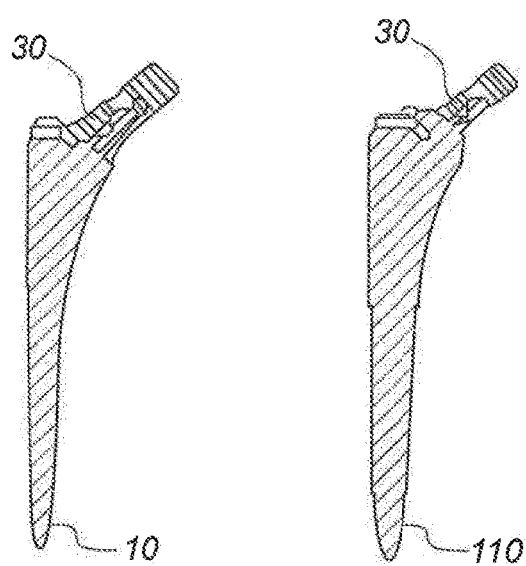
FIG. 1b illustrates the assembly formed between the trial standard offset femoral neck component and both the size 0 and size 10 broaches.

FIG. 1(b) shows the assembly of the trial standard offset femoral neck component 30 with the first and second broaches 10, 110, respectively. As can be seen from a comparison of the assemblies, the neck length (N) is longer when the neck component 30 is assembled on the second broach 110 as compared to when the neck component 30 is assembled on the first broach 10. This is because the trial standard offset femoral neck is spaced away from proximal surface 114 of the second broach 110 by the length of the platform 18 on the second broach 110. The provision of progressively longer platforms on progressively larger sizes of broach within a kit can therefore provide progressively longer neck lengths when using the same trial standard offset femoral neck component.

Figure 2A:
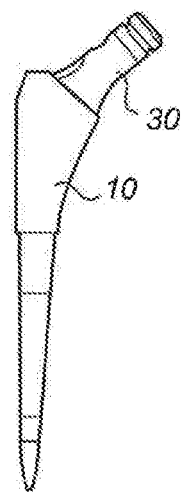
FIG. 2a shows a side view of one of the assemblies of FIG. 1b with the size 0 broach assembled with the standard offset trial femoral neck component.
Figure 2B:
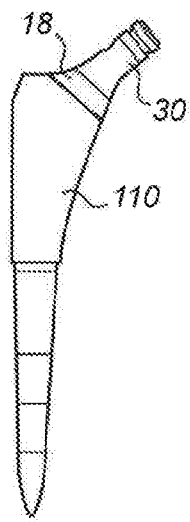
FIG. 2b shows a side view of the other one of the assemblies of FIG. 1b with the size 10 broach assembled with the standard offset trial femoral neck component.

FIGS. 2a and 2b show side views of the assemblies of FIG. 1b. The provision of a platform on the second broach (FIG. 2b), a feature which is absent on the first broach (FIG. 2a), results in the trial standard offset femoral neck component 30 sitting spaced further apart from the proximal surface of the broach when it is assembled with the second broach, than when it is assembled with the first broach. Consequently, the neck length of the trial standard offset trial femoral neck is longer.

This exemplary construction of the kit of the invention has been described for use in selecting the correct neck length of a final standard offset femoral neck component by using the same trial standard offset femoral neck component on different sizes of broach. The kit may also include, or alternatively the standard offset femoral neck component may be substituted by, a trial high offset femoral neck component. This high offset component can form an assembly with the first and second broaches in a similar manner as described for the trial standard offset neck component. The neck length of such an assembly can therefore be altered as discussed above in relation to the trial standard offset neck component. This allows the selection of the appropriate neck length of the final high offset femoral neck component.

Figure 3B:
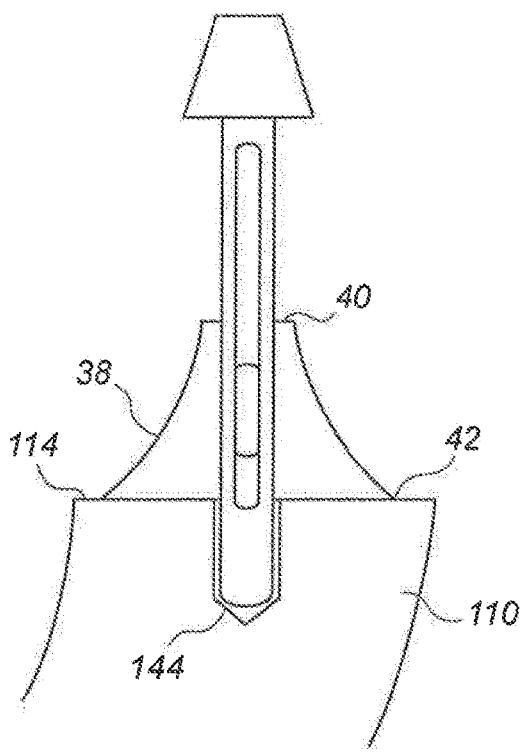

An example construction of a shoulder component 38 for use with a trial femoral neck component 16 is shown in FIGS. 3(a) and 3(b). The shoulder component has a first end 40 and a second end 42. The shoulder component has a flared shape, with the second end being wider than the first end. The shoulder component is oriented on the femoral neck component such that the wider second end is adjacent to the proximal surface 14, 114 of a broach 10, 110. The first broach 10 has a male connection feature (here shown as a recess 44 in the proximal surface) that is deeper than the corresponding male connection feature 144 in the second broach 110. The shoulder component is cannulated, allowing movement of the shoulder component along a longitudinal axis X of the neck component. In FIG. 3a the first end 40 of the shoulder component is positioned adjacent to the trunnion 44 (which forms a connection with the femoral head component) and the second end 42 is positioned adjacent to the proximal surface 14 of the first broach 10. In FIG. 3b, because the neck length is longer when the trial femoral neck component is mated with the second broach 110 (due to the shallower recess in the proximal surface of the second broach) than the first broach 10, the shoulder component is moved downwardly along the shaft of the neck component such that the second end 42 is positioned adjacent to the proximal surface of the second broach 110. This better recreates the geometry of the final implant, thereby improving the accuracy of the range of motion testing. The shoulder component can be a friction-fit on the shaft, such that the user slides the shoulder component down the shaft until the second end 42 is positioned adjacent to the proximal surface of the second broach 110. In other constructions, the shoulder component may be a loose-fit on the shaft, such that gravity causes the shoulder component to slide down the shaft until the second end 42 is positioned adjacent to the proximal surface of the second broach 110.

Figure 4B:
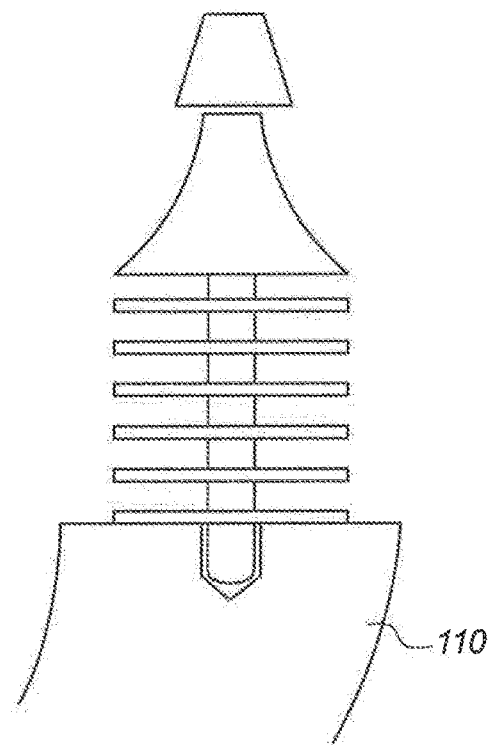

FIGS. 4a and 4b shows a second construction of the shoulder component 138 for use with the trial femoral neck component 16. The shoulder component has a first end 124 and a second end 126. The shoulder component has a flared shape, with the second end being wider than the first end. The distal portion 132 has a concertina-form. For example, the concertina-portion may be in the form of a spring. In FIG. 4a the first end 124 is positioned adjacent to the trunnion 130 (which forms a connection with the femoral head component) and the second end 126 is positioned adjacent to the proximal surface of the first broach 10. In FIG. 4b, because the neck length is longer when the trial femoral neck component is mated with the second broach 110, the distal portion 132 of the shoulder component expands so that the second end 126 is positioned adjacent to the proximal surface of the second broach 110. This better recreates the geometry of the final implant, thereby improving the accuracy of the range of motion testing.

As shown in FIG. 5, three configurations of an instrument kit can be provided, each configuration including three sizes of broach 210. Each broach includes two laterally spaced recesses 212, 214 provided within its proximal surface 216. The kit also includes three different trial femoral neck components 300 (3-5; 6-8 and 9-11). In each configuration, the same trial femoral neck component can be connected to each of the three broaches. Depending upon which recess 212, 214 the trial femoral neck component is connected into, the user can configure the assembly to have a standard neck offset or a high neck offset.

A schematic illustrating the mechanism of connection of a single trial femoral neck component 300 into a broach 210 to provide either a standard offset or a high offset is provided in FIGS. 6a, 6b, 6c and 6d. In FIGS. 6a and 6b, a 3-5 standard femoral neck component is mated with a first recess 212 within the proximal surface of the broach. In FIGS. 6c and 6d, the same 3-5 standard femoral neck component is mated with a second recess 214 that is laterally spaced apart from the first recess on the proximal surface of the broach. This second configuration provides a high offset femoral neck component.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the claims.

The invention claimed is:

1. A kit for use in selecting a femoral neck component of an orthopaedic joint prosthesis, the kit comprising:
   a first and a second broach, each of the first and second broaches having a neck connection element comprising a projection extending from a proximal surface of the broach, each projection having a length, the projection on the first broach having a different length than the projection on the second broach, and
   a trial femoral neck component having a neck connection element in the form of a recess in a distal surface, the recess being configured to mate with the projection on each of the first or second broaches such that mating of the trial femoral neck component with the first broach provides an assembly with a first neck length, and in which the mating of the trial femoral neck component with the second broach provides an assembly with a second neck length.

2. The kit according to claim 1, in which the trial femoral neck component includes a shaft having a longitudinal axis and a flared shoulder component, the flared shoulder component having a first end and a second end, said second end being wider than said first end and being oriented on the shaft such that the second end is distally located, and in which at least a portion of the shoulder component is moveable along the longitudinal axis of the shaft such that the second end is positionable adjacent to the proximal surface of the broach.

3. The kit according to claim 1, in which the kit includes two said trial femoral neck components, including a standard offset femoral neck trial component and a high offset femoral neck trial component.

4. The kit according to claim 1, in which the second broach is larger than the first broach, the projection on the second broach being longer than the projection on the first broach, such that a distal surface of the trial femoral neck component is spaced apart from the proximal surface of the first broach a first distance when the projection on the first broach is received within the recess of the trial femoral neck component, and the distal surface of the trial femoral neck component is spaced apart from the proximal surface of the second broach a second distance when the projection on the second broach is received within the recess of the trial femoral neck component, the second distance being greater than the first distance, the second broach thereby providing an assembly with a longer neck length.

5. The kit according to claim 4, in which the projection extending from the proximal surface of each of the first and second broaches includes a post configured to mate with the recess on the trial femoral neck component.

6. The kit according to claim 1, in which the second broach is larger than the first broach, the projection on each broach having a portion configured to be received with the recess in the trial femoral neck component, and in which the projection on at least one of the first and second broaches further comprises a platform provided adjacent to the proximal surface of the broach such that a distal surface of the trial femoral neck component is spaced apart from the proximal surface of the broach by the platform, thereby providing an assembly with a longer neck length.

7. The kit according to claim 6, in which the projection on each of the first and second broaches comprises a platform, the platform on the second broach having a greater length than the platform on the first broach.

8. The kit according to claim 1, in which the projection is configured for connection with a broach handle.

9. The kit according to claim 1, in which the kit consists of a single trial femoral neck component that includes a first recess and second recess each being configured for mating with the projection on the first or second broach, in which mating of the projection in the first recess creates an assembly with a femoral neck component having a first horizontal offset, and mating of the projection in the second recess creates an assembly with a femoral neck component having a second first horizontal offset.

10. The kit according to claim 9, in which the first horizontal offset is a standard offset and the second horizontal offset is a high offset.

11. A method of selecting a femoral neck component for use in an orthopaedic joint prosthesis, the method comprising the step of:
   (i) using a kit comprising a first and a second broach, each of the first and second broaches having a neck connection element comprising a projection extending from a proximal surface of the broach, each projection having a length, the projection on the first broach having a different length than the projection on the second broach, and a trial femoral neck component having a neck connection element in the form of a recess configured to mate with the projection on each of the first or second broaches such that mating of the trial femoral neck component with the first broach provides an assembly with a first neck length, and in which the mating of the trial femoral neck component with the second broach provides an assembly with a second neck length;

(ii) broaching a patient's femur using at least one of the first or second broaches;

(iii) retaining the broach within the patient's femur;

(iv) connecting the trial femoral neck component to the first broach or to the second broach;

(v) connecting a trial femoral head component to the trial femoral neck component; and (vi) performing a trial reduction.

12. The method according to claim 11, in which the trial femoral neck component connected to the first or second broach is a standard offset femoral neck trial component or a high offset femoral neck trial component.

13. A method of selecting a femoral neck component for use in an orthopaedic joint prosthesis, the method comprising the step of:

(i) using a kit comprising:

a broach having a neck connection element comprising a projection extending from a proximal surface of the broach, and a trial femoral neck component having a neck connection element in the form of a first recess and a second recess in a distal surface of the neck component, the first and second recesses being laterally spaced apart on the distal surface, each recess being configured to mate with the projection on the broach, such that mating of the projection on the broach with the first recess on the trial femoral neck component provides an assembly with a first horizontal offset, and in which the mating of the projection on the broach with the second recess on the trial femoral neck component provides an assembly with a second horizontal offset;

(ii) broaching a patient's femur using the broach;

(iii) retaining the broach within the patient's femur;

(iv) connecting the trial femoral neck component to the broach by mating the projection on the broach with one of the first recess or the second recess on the trial femoral neck component to provide a trial femoral neck component with a first horizontal offset;

(v) connecting a trial femoral head component to the trial femoral neck component; and (vi) performing a trial reduction.

14. The method of claim 13, further comprising the steps of:

(vii) disconnecting the trial femoral neck component from the broach;

(viii) reconnecting the trial femoral neck component with the broach by mating the projection on the broach with the other one of the first or second recesses on the trial femoral neck component to form a trial femoral neck component with a second horizontal offset;

(ix) connecting a trial femoral head component to the trial femoral neck component; and (x) performing a trial reduction.

15. The method according to claim 13, in which the first horizontal offset is one of a standard offset or a high offset, and the second horizontal offset is the other one of the standard offset and the high offset.

* * * * *